United States Patent
Wang et al.

(10) Patent No.: US 10,154,967 B2
(45) Date of Patent: Dec. 18, 2018

(54) 2,2',6,6'-TETRAISOPROPYL-4,4'-BIPHENOL LIPID MICROSPHERE PREPARATIONS AND PREPARATION METHODS THEREFOR

(71) Applicant: XI'AN LIBANG PHARMACEUTICAL CO., LTD, Xi'an, Shaanxi (CN)

(72) Inventors: Rutao Wang, Xi'an (CN); Tao Chen, Xi'an (CN); Shupan Guo, Xi'an (CN); Huijing Hu, Xi'an (CN); Long An, Xi'an (CN); Weijiao Wang, Xi'an (CN)

(73) Assignee: XI'AN LIBANG PHARMACEUTICAL CO., LTD, Xi'an (CN)

( * ) Notice: Subject to any disclaimer, the term of this patent is extended or adjusted under 35 U.S.C. 154(b) by 0 days.

(21) Appl. No.: 15/141,517

(22) Filed: Apr. 28, 2016

(65) Prior Publication Data

US 2016/0235684 A1   Aug. 18, 2016

Related U.S. Application Data

(63) Continuation of application No. 14/374,220, filed as application No. PCT/CN2012/072031 on Mar. 7, 2012, now abandoned.

(30) Foreign Application Priority Data

Feb. 6, 2012 (CN) .......................... 2012 1 0025611

(51) Int. Cl.
| | |
|---|---|
| A61K 9/107 | (2006.01) |
| A61K 31/05 | (2006.01) |
| A61K 9/50 | (2006.01) |
| A61K 9/00 | (2006.01) |
| A61K 9/16 | (2006.01) |
| A61K 47/44 | (2017.01) |
| A61K 47/12 | (2006.01) |
| A61K 47/24 | (2006.01) |
| A61K 47/02 | (2006.01) |
| A61K 47/10 | (2017.01) |
| A61K 47/18 | (2017.01) |
| A61K 47/22 | (2006.01) |

(52) U.S. Cl.
CPC .......... *A61K 9/5015* (2013.01); *A61K 9/0019* (2013.01); *A61K 9/1075* (2013.01); *A61K 9/16* (2013.01); *A61K 9/5089* (2013.01); *A61K 31/05* (2013.01); *A61K 47/02* (2013.01); *A61K 47/10* (2013.01); *A61K 47/12* (2013.01); *A61K 47/183* (2013.01); *A61K 47/22* (2013.01); *A61K 47/24* (2013.01); *A61K 47/44* (2013.01)

(58) Field of Classification Search
CPC ........................................................ A61K 9/10
See application file for complete search history.

(56) References Cited

U.S. PATENT DOCUMENTS

| | | | |
|---|---|---|---|
| 5,714,520 A | 2/1998 | Jones et al. | |
| 6,572,884 B1 * | 6/2003 | Pai .......................... | A61K 33/24 424/455 |
| 2002/0025337 A1 * | 2/2002 | Illum .................... | A61K 9/1075 424/450 |
| 2004/0137049 A1 * | 7/2004 | Pai ...................... | A61K 9/0019 424/450 |
| 2004/0225022 A1 | 11/2004 | Desai | |
| 2006/0148776 A1 | 7/2006 | Ulm et al. | |
| 2007/0026058 A1 | 2/2007 | Pereswetoff-Morath et al. | |
| 2014/0370101 A1 | 12/2014 | Wang et al. | |

FOREIGN PATENT DOCUMENTS

| | | | |
|---|---|---|---|
| CN | 1478465 A | 3/2004 | |
| CN | 101804043 * | 8/2010 | ............ A61K 31/53 |
| CN | 101804043 A | 8/2010 | |
| WO | WO 2007/052288 A2 | 5/2007 | |

OTHER PUBLICATIONS

Ogata et al., Bio. Pharm. Bull., 2007, 30(8), pp. 1565-1568.*
Barros et al. (2007). "Effects of the vitamin E in catalase activities in hippocampus after status epilepticus induced by pilocarpine in Wistar rats." Neuroscience Letters, 416: 227-230.
Ogata et al. (2005). "Mechanism of Action of Dipropofol and Synergistic Action with Other Antibacterial Agents in Vitro." Biol. Pharm. Bull, 28(9): 1773-1775.
Ogata et al. (2007). "Solubilization of Dipropofol, and Antibacterial Agent, Using Saccharide and Ascorbic Acid." Biol. Pharm. Bull, 30(8): 1565-1568.
Ogunmekan et al. (1989). "A Randomized, Double-Blind, Placebo-Controlled, Clinical Trial of D-a-Tocopheryl Acetate (Vitamin E), as Add-On Therapy, for Epilepsy in Children." Epilepsia, 30(1):84-89.
United States Patent and Trademark Office, Office Action for U.S. Appl. No. 14/374,220, dated Sep. 25, 2015, 11 pages, U.S.A.
United States Patent and Trademark Office, Office Action for U.S. Appl. No. 14/374,220, dated Dec. 9, 2014, 12 pages, U.S.A.
United States Patent and Trademark Office, Office Action for U.S. Appl. No. 14/374,220, dated Feb. 1, 2016, 10 pages, U.S.A.
United States Patent and Trademark Office, Office Action for U.S. Appl. No. 14/374,220, dated Feb. 4, 2015, 6 pages, U.S.A.
Extended European Search Report from corresponding European Patent Application No. 12868324.0 dated Jun. 8, 2015, 4 pages.
International Search Report and Written Opinion from International Patent Application No. PCT/CN2012/072031, dated Nov. 15, 2012, 9 pages.

* cited by examiner

*Primary Examiner* — Brian Gulledge
(74) *Attorney, Agent, or Firm* — Alston & Bird LLP

(57) ABSTRACT

This invention relates to a 2,2',6,6'-tetraisopropyl-4,4'-biphenol lipid microsphere preparation having 2,2',6,6'-tetraisopropyl-4,4'-biphenol as its active ingredient and formed into said lipid microsphere preparation with common medically used injection-grade oil, emulsifier, and injection-grade water.

8 Claims, No Drawings

2,2',6,6'-TETRAISOPROPYL-4,4'-BIPHENOL LIPID MICROSPHERE PREPARATIONS AND PREPARATION METHODS THEREFOR

CROSS-REFERENCE TO RELATED APPLICATIONS

This application is a continuation of U.S. patent application Ser. No. 14/374,220, filed Jul. 23, 2014; which application is a U.S. National Stage Application, filed under 35 U.S.C. § 371, of International Application No. PCT/CN2012/072031, filed Mar. 7, 2012, which application further claims priority to Chinese Application No. 201210025611.2, filed Feb. 6, 2012; the contents of all of which as are hereby incorporated by reference in their entirety.

FIELD OF THE INVENTION

This invention relates to 2,2',6,6'-tetraisopropyl-4,4'-biphenol lipid microsphere preparations and the preparation methods therefor, in the field of pharmaceutical preparations.

BACKGROUND OF THE INVENTION 2,2',6,6'-tetraisopropyl-4,4'-biphenol (hereinafter referred to as biphenol) is an anti-epileptic compound newly developed (Chinese patent CN 101804043A, Uses of biphenol and its derivatives in drugs for the treatment of epilepsy) for treating many epileptic symptoms such as generalized tonic-clonic seizures (grand mal), absence seizures (petit mal), simple partial seizures, complex partial seizures (psychomotor seizures), autonomic seizures (periodic seizures) and others. Experimental studies have shown that biphenol has a strong affinity towards GABA receptors and is a GABA agonist, while it is an antagonist for NMDA receptors for regulating the $Ca^{2+}$ influx in $Ca^{2+}$ channels. Biphenol also offers protection against the excitotoxic effect induced by kainate (kainic acid). Studies have confirmed that biphenol is a significantly stronger antioxidant than propofol and has a stronger protective effect on the brain. Of particular importance is that biphenol does not cause the patients to lose consciousness and therefore has important clinical values in the treatment of patients with different types of epilepsy.

However, biphenol is a highly lipid soluble compound that is difficult to dissolve in water. Studies have shown that it is difficult to achieve a desired effect by using surfactants such as cyclodextrin, Tween 80, $V_c$ or DMSO to assist or increase its dissolution and, thereby, its efficacy is affected and its clinical application becomes limited. In this invention, lipid microspheres are used as a drug carrier for the biphenol. This not only overcomes the problems due to insolubility of biphenol, but also allows the drug to be selectively accumulated in a lesion site and maximizes the amount of drug that is delivered to a targeted site so that the concentration of the drug at that site can be increased by several to hundred times above that of conventional preparations to improve its therapeutic effect. At the same time, there is minimal amount of drugs distributed in healthy tissues such that any cytotoxic side effects and adverse reactions are significantly reduced, and hence high efficacy with low toxicity would be achieved. Currently, there has been no report on biphenol lipid microsphere preparations. Therefore, the rational formulation of a preparation based on the physiochemical properties of biphenol for safe, stable and effective biphenol lipid microspheres is an issue this invention will address.

The present invention provides a 2,2',6,6'-tetraisopropyl-4,4'-biphenol lipid microsphere preparation and its preparation method. 0.5~1% of antioxidants were added to the preparation to address the issue that biphenol is easily oxidizable. Particularly, vitamin E, a potent, lipid soluble antioxidant, is used for ensuring the stability of the drug in the preparation. This invention uses only phospholipid emulsifiers in an amount of 1 to 1.5% without any co-solvent so as to prevent hemolysis and production of substances that may otherwise cause thrombotic inflammation. Further, the emulsifiers of this invention are egg lecithin derived from the yolk of animal embryos which are easier and safer to be absorbed by the human body.

SUMMARY OF THE INVENTION

The present invention provides a 2,2',6,6'-tetraisopropyl-4,4'-biphenol lipid microsphere preparation, and preparation method therefor.

The lipid microsphere preparations of this invention are prepared by the processing of active ingredients comprising 2,2',6,6'-tetraisopropyl-4,4'-biphenol (hereinafter referred as biphenol), injection-grade oil, emulsifier, and injection-grade water. In a specific embodiment, 0.1~3% of biphenol, 10~30% of injection-grade oil, 1~1.5% of emulsifiers, 0.5~1% of antioxidants, 0~5% of additives with the remaining being injection-grade water. All units are in percentage by weight.

The chemical structure of said biphenol is:

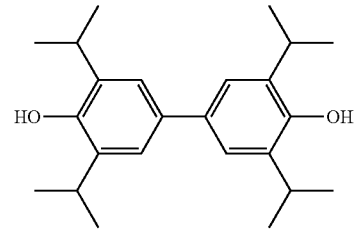 [SMILES: CC(C)c1cc(-c2cc(C(C)C)c(O)c(C(C)C)c2)cc(C(C)C)c1O]

The injection-grade oil is selected from one or more of soybean oil, medium chain triglyceride oil, sea buckthorn oil, and tea oil.

The emulsifier is selected from one or more of soy lecithin, hydrogenated lecithin, synthetic lecithin, and egg lecithin.

The antioxidant is selected from one or more of vitamin E, ascorbic acid, and sodium hydrogen sulfite.

The additive is selected from one or more of pH adjusting agent, tonicity adjusting agents, complexing agents; said pH adjusting agent is hydrochloric acid or sodium hydroxide; said tonicity adjusting agent is glycerin; said complexing agent is EDTA; wherein their percentage by weight in an injection preparation are 0.01 to 1%, 0.1~2.5% and 0.01 to 1% respective.

Preferably, the lipid microsphere preparation of this invention has the following composition.

Every 100 ml of lipid microsphere preparation comprises 1000 mg of biphenol, 10 g of soybean oil, 1.2 g of injection-grade egg lecithin, 1 g of vitamin E, 2.5 g of glycerin, 0.5 g EDTA, and the remaining being injection-grade water.

Other preferred embodiments for the lipid microsphere preparation of this invention are disclosed in the Examples.

This invention also aims to provide a method for preparing biphenol lipid microsphere preparations.

The preparation method of this invention comprises the following steps:
1) Dissolving the emulsifiers completely with the injection-grade oil under a nitrogen atmosphere and in a 70° C. water bath; adding the antioxidants with stirring for dissolution before adding the biphenol with heat and stirring for dissolution to obtain an oil phase;
2) Dissolving the tonicity adjusting agents and the complexing agents in the injection-grade water to obtain an aqueous phase;
3) Adding the oil phase slowly to the aqueous phase while shearing under nitrogen for 5 minutes to obtain a preliminary emulsion;
4) Homogenizing the preliminary emulsion with a high-pressure homogenizer before filtering with a microporous membrane filter, flushing with nitrogen, sealing and autoclaving at 115° C. to form the final product.

In the present invention, due to differences in water-solubility of antioxidants, there are different ways for adding the antioxidants. Lipid-soluble antioxidants are added to the oil phase while water-soluble antioxidants are added to the aqueous phase.

In a specific embodiment, said method for preparing biphenol lipid microsphere preparations comprises the following steps:
1) Weighing the raw materials: 1 g~30 g of biphenol, 100 ml 300 ml injection-grade oil, 25 g of glycerin, 10 g~15 g of emulsifiers, 5 g~10 g of antioxidants, with the remaining being injection-grade water.
2) Dissolving the emulsifiers and the antioxidants (Vitamin E) completely with the injection-grade oil under a nitrogen atmosphere and in a 70° C. water bath, before adding the biphenol with heat and stirring for dissolution to obtain an oil phase;
3) Dissolving the glycerin and the complexing agents in the injection-grade water and stir to obtain an aqueous phase;
4) Adding the oil phase slowly to the aqueous phase while shearing under nitrogen (10000 r, 5 min) to obtain a preliminary emulsion, and adjusting the pH to around 8.0 with NaOH;
5) Homogenizing the preliminary emulsion 5~8 times with a high-pressure homogenizer at 800~900 bar before filtering with a microporous membrane filter, flushing with nitrogen, sealing and autoclaving at 115° C. to obtain the final product (1000 ml).

In another specific embodiment, said method for preparing biphenol lipid microsphere preparations comprises the following steps:
1) Weighing the raw materials: 1 g~30 g biphenol, 100 ml 300 ml injection-grade oil, 25 g of glycerin, 10 g~15 g of emulsifiers, 5 g~10 g of antioxidants, with the remaining made up of injection-grade water.
2) Dissolving the emulsifier completely in the injection-grade oil under a nitrogen atmosphere and in a 70° C. water bath before adding the biphenol with heat and stirring for dissolution to obtain an oil phase;
3) Dissolving the glycerin, the antioxidants (ascorbic acid or sodium bisulfite) and the complexing agents in injection-grade water and stirring to obtain an aqueous phase;
4) Adding the oil phase slowly to the aqueous phase while shearing under nitrogen (10000 r, 5 min) to obtain a preliminary emulsion, and adjusting pH to around 8.0 with NaOH;
5) Homogenizing the preliminary emulsion 5~8 times with a high-pressure homogenizer at 800~900 bar before filtering with a microporous membrane filter, flushing with nitrogen, sealing and autoclaving at 115° C. to obtain the final product (1000 ml).

Other embodiments of the preparation method of this invention are disclosed in the Examples.

The preparation of this invention is a lipid microsphere preparation for use in intravenous injections.

The particle size of the lipid microspheres of this invention is in the range of 100 nm~800 nm with the average particle size being 150 nm~300 nm.

In the preparation of this invention, biphenol is encapsulated within lipid microspheres which greatly increase its solubility in water, the amount of drug that can be loaded, and also the stability of the preparation. Further, being a novel drug carrier, lipid microspheres are non-toxic, non-immunogenic, reducing irritation due to the drug and decreasing the drug's toxic side effects.

This invention increases the stability of the injection, extends the drug's shelf life, improves its solubility and ensures its safeness. Moreover, the simple and feasible preparation process of the present invention is time and cost effective such that it is well suited for mass production. Furthermore, the formula and preparation methods for the preparation of this invention have been scientifically screened and proven.

The preparation of this invention relates to anti-epileptic preparations.

The anti-epileptic preparation of this invention has significantly higher efficacy in comparison to CMCNa-biphenol.

In this invention, the method for administering the drug is switched from oral administration to intravenous injection which improves drug absorption and increases the therapeutic effect of the drug;

Detailed experimental results on the anti-epileptic effect of the preparation of this invention can be found in the Examples.

Obviously, further embodiments can be devised by means of modification, replacement or alteration of the invention described above with common knowledge and skills in the art without steering away from the basic concepts of this invention.

The following specific embodiments in the Examples aim to provide further explanation of the above description. One should not interpret this as a means to limit the scope of this invention to only the embodiments which follow. All embodiments based on the above description should fall into the scope of this invention.

DETAILED DESCRIPTION OF THE INVENTION

The following examples further illustrate the present invention but in no way limit the scope of the present invention. Those skilled in the art will appreciate that the present invention is not limited to the embodiments and methods of preparation described with reference to the following examples. Further, those equivalent embodiments that skilled person in the art can make by modification, replacement or alteration of the present invention should also fall into the scope of the present invention.

Part 1) Lipid Microsphere Preparation Prepared with Different Concentrations of Biphenol Example 1: 1% Biphenol Lipid Microsphere Preparation

| Drugs and Excipients | Amount (g) |
| --- | --- |
| Biphenol | 10.0 |
| Injection-grade Soybean oil | 100 |
| Egg lecithin | 12 |
| Vitamin E | 10 |
| Glycerin | 25 |
| EDTA | 5 |
| Injection-grade water | Make up to 1000 ml |

Preparation Method 1) 12 g of egg lecithin was completely dissolved in 100 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtained an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 2: 0.1% Biphenol Lipid Microsphere Preparation

| Drugs and Excipients | Amount (g) |
| --- | --- |
| Biphenol | 1.0 |
| Injection-grade Sea buckthorn oil | 100 |
| Hydrogenated Lecithin | 12 |
| Ascorbic acid | 10 |
| Glycerin | 25 |
| EDTA | 5 |
| Injection-grade water | Make up to 1000 ml |

Preparation Method 1) 12 g of hydrogenated lecithin was completely dissolved in 100 g of injection-grade oil under a nitrogen atmosphere and in a 70° C. water bath. 1 g of biphenol was then added and nitrogen gas was fed in for protection before being dissolved, with heat and stirring, to obtain an oil phase.

2) 25 g of glycerin, 10 g ascorbic acid and 5 g of EDTA were dissolved, with stirring, in the injection-grade water to obtain the aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 3: 3% Biphenol Lipid Microsphere Preparation

| Drugs and Excipients | Amount (g) |
| --- | --- |
| Biphenol | 30 |
| Injection-grade Medium-chain triglyceride oil | 100 |
| Soy lecithin | 12 |
| Sodium bisulfite | 10 |
| Glycerin | 25 |
| EDTA | 5 |
| Injection-grade water | Make up to 1000 ml |

Preparation Method 1) 12 g of soy lecithin was completely dissolved in 100 g of injection-grade oil under a nitrogen atmosphere and in a 70° C. water bath. 30 g of biphenol was then added and nitrogen gas was fed in for protection before being dissolved, with heat and stirring, to obtain an oil phase.

2) 25 g of glycerin, 10 g of sodium bisulfite and 5 g of EDTA were dissolved, with stirring, in the injection-grade water to obtained an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Part 2) Lipid Microsphere Preparation Prepared with Different Types of Injection Oil and Contents Example 4: Lipid Microsphere Preparation with 20% Soybean Oil

| Drugs and Excipients | Amount (g) |
| --- | --- |
| Biphenol | 10.0 |
| Injection-grade Soybean oil | 200 |
| Egg lecithin | 12 |
| Vitamin E | 10 |
| Glycerin | 25 |
| EDTA | 5 |
| Injection-grade water | Make up to 1000 ml |

Preparation Method 1) 12 g of egg lecithin was completely dissolved in 200 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain the aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 5: Lipid Microsphere Preparation with 10% Medium-Chain Glyceride Oil

| Drugs and Excipients | Amount (g) |
| --- | --- |
| Biphenol | 10.0 |
| Injection-grade Medium chain triglyceride oil | 100 |
| Egg lecithin | 12 |
| Vitamin E | 10 |
| Glycerin | 25 |
| EDTA | 5 |
| Injection-grade water | Make up to 1000 ml |

Preparation Method 1) 12 g of egg lecithin was completely dissolved in 100 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 6: Lipid Microsphere Preparation with 30% Sea Buckthorn Oil

| Drugs and Excipients | Amount (g) |
| --- | --- |
| Biphenol | 10.0 |
| Injection-grade Sea buckthorn oil | 300 |
| Egg lecithin | 12 |
| Vitamin E | 10 |
| Glycerin | 25 |
| EDTA | 5 |
| Injection-grade water | Make up to 1000 ml |

Preparation Method 1) 12 g of egg lecithin was completely dissolved in 300 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 7: Lipid Microsphere Preparation with 10% Tea Oil

| Drugs and Excipients | Amount (g) |
| --- | --- |
| Biphenol | 10.0 |
| Injection-grade Tea oil | 100 |
| Egg lecithin | 12 |
| Vitamin E | 10 |
| Glycerin | 25 |
| EDTA | 5 |
| Injection-grade water | Make up to 1000 ml |

Preparation Method 1) 12 g of egg lecithin was completely dissolved in 100 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Part 3) Lipid Microsphere Preparations with Different Type and Amount of Emulsifier

Example 8: Lipid Microsphere Preparation with 1% Egg Lecithin

| Drugs and Excipients | Amount (g) |
| --- | --- |
| Biphenol | 10.0 |
| Injection-grade Soybean oil | 100 |
| Egg lecithin | 10 |
| Vitamin E | 10 |
| Glycerin | 25 |
| EDTA | 5 |
| Injection-grade water | Make up to 1000 ml |

Preparation Method 1) 10 g of egg lecithin was completely dissolved in 100 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 9: Lipid Microsphere Preparation with 1.5% Soy Lecithin

| Drugs and Excipients | Amount (g) |
| --- | --- |
| Biphenol | 10.0 |
| Injection-grade Soybean oil | 300 |
| Soy lecithin | 15 |
| Vitamin E | 10 |
| Glycerin | 25 |
| EDTA | 5 |
| Injection-grade water | Make up to 1000 ml |

Preparation Method 1) 15 g of egg lecithin was completely dissolved in 100 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 10: Lipid Microsphere Preparation with 1.2% Hydrogenated Lecithin

| Drugs and Excipients | Amount (g) |
| --- | --- |
| Biphenol | 10.0 |
| Injection-grade Soybean oil | 100 |
| Hydrogenated Lecithin | 12 |
| Vitamin E | 10 |
| Glycerin | 25 |
| EDTA | 5 |
| Injection-grade water | Make up to 1000 ml |

Preparation Method 1) 12 g of hydrogenated lecithin was completely dissolved in 100 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 11: Lipid Microsphere Preparation with 1.2% Synthetic Phospholipid

| Drugs and Excipients | Amount (g) |
| --- | --- |
| Biphenol | 10.0 |
| Injection-grade Soybean oil | 100 |
| Synthetic phospholipid | 12 |
| Vitamin E | 10 |
| Glycerin | 25 |
| EDTA | 5 |
| Injection-grade water | Make up to 1000 ml |

Preparation Method 1) 12 g of synthetic phospholipid was completely dissolved in 100 g of injection-grade oil under a nitrogen atmosphere and in a 70° C. water bath. 10 g of biphenol and 10 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Part 4) Lipid Microsphere Preparation with Different Types and Amount of Antioxidant

Example 12: Lipid Microsphere Preparation with 0.5% Vitamin E

| Drugs and Excipients | Amount (g) |
| --- | --- |
| Biphenol | 10.0 |
| Injection-grade Soybean oil | 100 |
| Egg lecithin | 12 |
| Vitamin E | 5 |
| Glycerin | 25 |
| EDTA | 5 |
| Injection-grade water | Make up to 1000 ml |

Preparation Method 1) 12 g of egg lecithin was completely dissolved in 100 g of injection-grade oil under a nitrogen atmosphere and in a 70° C. water bath, 10 g of biphenol and 5 g of vitamin E were then added and nitrogen gas was fed in for protection before being dissolved, with heat and stirring, to obtain an oil phase.

2) 25 g of glycerin and 5 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 13: Lipid Microsphere Preparation with 1% Ascorbic Acid

| Drugs and Excipients | Amount (g) |
| --- | --- |
| Biphenol | 10.0 |
| Injection-grade Soybean oil | 100 |
| Egg lecithin | 12 |
| Ascorbic acid | 10 |
| Glycerin | 25 |
| EDTA | 5 |
| Injection-grade water | Make up to 1000 ml |

Preparation Method 1) 12 g of egg lecithin was completely dissolved in 100 g of injection-grade oil under a nitrogen atmosphere and in a 70° C. water bath. 10 g of biphenol was then added and nitrogen gas was fed in for protection before being dissolved, with heat and stirring, to obtain an oil phase.

2) 25 g of glycerin, 5 g of EDTA and 10 g of ascorbic acid were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 14: Lipid Microsphere Preparation with 1% Sodium Bisulfite

| Drugs and Excipients | Amount (g) |
| --- | --- |
| Biphenol | 10.0 |
| Injection-grade Soybean oil | 100 |
| Egg lecithin | 12 |
| Sodium bisulfite | 10 |
| Glycerin | 25 |
| EDTA | 5 |
| Injection-grade water | Make up to 1000 ml |

Preparation Method 1) 12 g of egg lecithin was completely dissolved in 100 g of injection-grade oil under a nitrogen atmosphere and in a 70° C. water bath. 10 g of biphenol was then added and nitrogen gas was fed in for protection before being dissolved, with heat and stirring, to obtain an oil phase.

2) 25 g of glycerin, 5 g of EDTA and 10 g of sodium bisulfite were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Part 5) Lipid Microsphere Preparation with Different Types and Amount of Additives

Example 15: Lipid Microsphere Preparation with 1.5% Glycerin and 0.3% EDTA

| Drugs and Excipients | Amount (g) |
| --- | --- |
| Biphenol | 10.0 |
| Injection-grade Soybean oil | 100 |
| Egg lecithin | 12 |
| Vitamin E | 10 |
| Glycerin | 15 |
| EDTA | 3 |
| Injection-grade water | Make up to 1000 ml |

Preparation Method 1) 12 g of Egg Lecithin was Completely Dissolved in 100 g of injection-grade oil under a nitrogen atmosphere and in a 70° C. water bath. 10 g of biphenol and 10 g vitamin E were then added and nitrogen gas was fed in for protection before being dissolved, with heat and stirring, to obtain an oil phase.

2) 15 g of glycerin and 3 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 16: Lipid Microsphere Preparation with 2% Glycerin and 1% EDTA

| Drugs and Excipients | Amount (g) |
| --- | --- |
| Biphenol | 10.0 |
| Injection-grade Soybean oil | 100 |
| Egg lecithin | 12 |
| Vitamin E | 10 |
| Glycerin | 20 |
| EDTA | 10 |
| Injection-grade water | Make up to 1000 ml |

Preparation Method 1) 12 g of egg lecithin was completely dissolved in 100 g of injection-grade oil under a nitrogen atmosphere and in a 70° C. water bath. 10 g of biphenol and 5 g vitamin E were then added and nitrogen gas was fed in for protection before being dissolved, with heat and stirring, to obtain an oil phase.

2) 20 g of glycerin and 10 g of EDTA were dissolved, with stirring, in the injection-grade water to obtain an aqueous phase.

3) The oil phase was added slowly to the aqueous phase while sheared under nitrogen (10000 r, 5 min) to obtain a preliminary emulsion which was then adjusted to around pH 8.0 with sodium hydroxide.

4) The preliminary emulsion was homogenized with a high-pressure homogenizer for 5~8 times at 800~900 bar and filtered with a microporous membrane filter before being flushed with nitrogen, sealed, autoclaved at 115° C. to obtain the final product.

Example 17: Experiment for Screening of Formulations

1) Selection of Injection-Grade Oil

This experiment was conducted with biphenol lipid microsphere preparations prepared separately with soybean oil, medium chain triglyceride oil, sea buckthorn oil and tea oil. The final emulsions appeared homogenous with no layering or floating oil. 1 ml of each of the lipid microsphere injections was obtained separately and diluted by a factor of 1000 and their particle sizes were determined by dynamic light scattering particle size analyzer (Marvelen, US). Results showed that the particle sizes of the microspheres prepared using the above mentioned injection-grade oil were evenly distributed with 70% having a particle size smaller than 500 nm and 100% having a particle size smaller than 1 μm which fulfilled the requirement for a lipid microsphere preparation to be used for intravenous injections. Soybean oil and medium chain triglyceride oil fared the best with 90% having a particle size smaller than 500 nm and 100% having a particle size smaller than 1 μm.

2) Selection of Emulsifier

This experiment was conducted with biphenol lipid microsphere preparations prepared separately with egg lecithin, soy lecithin and hydrogenated lecithin. The final emulsions appeared homogenous with no layering or floating oil. 1 ml of each of the lipid microsphere injections was obtained separately and diluted by a factor of 1000 and their particle sizes were determined by dynamic light scattering particle size analyzer (Marvelen, US). Results showed that the particle sizes of the microspheres prepared using the above mentioned injection-grade oil were evenly distributed with 70% having a particle size smaller than 500 nm and 100% having a particle size smaller than 1 μm which fulfilled the requirement for a lipid microsphere preparation to be used for intravenous injections.

3) Selection of Tonicity Adjusting Agent

This experiment was conducted with glycerin as the tonicity adjusting agent so as to ensure that the microspheres would be isotonic inside the human body. The osmolarity of the final emulsion was determined to be 300~400 mOsm/L by an osmometer (freezing point depression method) which fulfilled the requirement for a lipid microsphere preparation to be used for intravenous injection.

4) Antioxidant

This experiment was conducted with vitamin E as the antioxidant so as to prevent any instability due to oxidation. The final emulsions appeared homogenous with no layering or floating oil. 1 ml of the lipid microsphere injections was obtained separately and diluted by a factor of 1000 and the particle size was determined by dynamic light scattering particle size analyzer (Marvelen, US). Results showed that the microspheres obtained with the above mentioned injection-grade oil was evenly distributed with 70% having a particle size smaller than 500 nm and 100% having a particle size smaller than 1 μm which fulfills the requirement for a lipid microsphere preparation to be used in intravenous injection.

5) Complexing Agent

This experiment was conducted with biphenol lipid microsphere preparations prepared with EDTA, a common complexing agent, so as to decrease the concentration of free positive ions in the microspheres and increase the stability of lipid microsphere preparation. The final emulsions appeared homogenous with no layering or floating oil. 1 ml of each of the lipid microsphere injections was obtained separately and diluted by a factor of 1000 and their particle sizes were determined by dynamic light scattering particle size analyzer (Marvelen, US). Results showed that the microspheres prepared using the above mentioned injection-grade oil were evenly distributed with 70% having a particle size smaller than 500 nm and 100% having a particle size smaller than 1 μm which fulfills the requirement for a lipid microsphere preparation to be used for intravenous injections.

The following experiments characterized the physio-chemical properties and safeness of the lipid microsphere preparation prepared in accordance to above description.

Experiment 1

Stability Test

The biphenol lipid microspheres prepared were kept at 4° C. for 6 months before subjected to 45° C. for 6 months and, after which, were placed at room temperature for 12 months. The stability of the products was evaluated in terms of their appearance, pH and encapsulation efficiency. Results are shown in Table 1.

TABLE 1

Results of the Stability Test on the biphenol lipid microspheres of this invention

| Sample | Time | Appearance | | | pH | | | Encapsulation efficiency | | |
|---|---|---|---|---|---|---|---|---|---|---|
| | | 4° C. | 25° C. | 45° C. | 4° C. | 25° C. | 45° C. | 4° C. | 25° C. | 45° C. |
| Example 1 | 0 mth | Homogenous | Homogenous | Homogenous | 7.85 | 7.86 | 7.84 | 98.45 | 98.35 | 98.46 |
| | 1 mth | Homogenous | Homogenous | Homogenous | 7.74 | 7.71 | 7.68 | 98.45 | 98.38 | 98.45 |
| | 2 mth | Homogenous | Homogenous | Homogenous | 7.66 | 7.64 | 7.55 | 98.40 | 98.36 | 98.44 |
| | 3 mth | Homogenous | Homogenous | Homogenous | 7.54 | 7.66 | 7.46 | 98.41 | 98.37 | 98.45 |
| | 6 mth | Homogenous | Homogenous | Homogenous | 7.32 | 7.52 | 7.29 | 98.38 | 98.25 | 98.36 |
| | 9 mth | — | Homogenous | — | — | 7.48 | — | — | 98.26 | — |
| | 12 mth | — | Homogenous | — | — | 7.31 | — | — | 98.23 | — |

TABLE 1-continued

Results of the Stability Test on the biphenol lipid microspheres of this invention

| Sample | Time | Appearance | | | pH | | | Encapsulation efficiency | | |
| --- | --- | --- | --- | --- | --- | --- | --- | --- | --- | --- |
| | | 4° C. | 25° C. | 45° C. | 4° C. | 25° C. | 45° C. | 4° C. | 25° C. | 45° C. |
| Example 3 | 0 mth | Homogenous | Homogenous | Homogenous | 7.94 | 7.84 | 7.91 | 98.54 | 98.38 | 98.44 |
| | 1 mth | Homogenous | Homogenous | Homogenous | 7.80 | 7.73 | 7.82 | 98.39 | 98.44 | 98.54 |
| | 2 mth | Homogenous | Homogenous | Homogenous | 7.74 | 7.66 | 7.60 | 98.39 | 98.45 | 98.33 |
| | 3 mth | Homogenous | Homogenous | Homogenous | 7.62 | 7.62 | 7.47 | 98.64 | 98.38 | 98.31 |
| | 6 mth | Homogenous | Homogenous | Homogenous | 7.39 | 7.53 | 7.33 | 98.55 | 98.31 | 98.35 |
| | 9 mth | — | Homogenous | — | — | 7.44 | — | — | 98.34 | — |
| | 12 mth | — | Homogenous | — | — | 7.28 | — | — | 98.29 | — |
| Example 6 | 0 mth | Homogenous | Homogenous | Homogenous | 7.88 | 7.92 | 7.93 | 99.12 | 98.85 | 98.65 |
| | 1 mth | Homogenous | Homogenous | Homogenous | 7.86 | 7.85 | 7.80 | 98.57 | 98.74 | 98.37 |
| | 2 mth | Homogenous | Homogenous | Homogenous | 7.79 | 7.81 | 7.74 | 98.65 | 98.75 | 98.29 |
| | 3 mth | Homogenous | Homogenous | Homogenous | 7.68 | 7.75 | 7.63 | 98.36 | 98.63 | 98.54 |
| | 6 mth | Homogenous | Homogenous | Homogenous | 7.59 | 7.62 | 7.44 | 98.54 | 98.68 | 98.47 |
| | 9 mth | — | Homogenous | — | — | 7.46 | — | — | 98.58 | — |
| | 12 mth | — | Homogenous | — | — | 7.31 | — | — | 98.71 | — |
| Example 8 | 0 mth | Homogenous | Homogenous | Homogenous | 7.87 | 7.93 | 7.89 | 99.02 | 98.99 | 98.66 |
| | 1 mth | Homogenous | Homogenous | Homogenous | 7.80 | 7.82 | 7.80 | 98.72 | 98.47 | 98.87 |
| | 2 mth | Homogenous | Homogenous | Homogenous | 7.76 | 7.79 | 7.77 | 98.56 | 98.65 | 98.25 |
| | 3 mth | Homogenous | Homogenous | Homogenous | 7.65 | 7.73 | 7.66 | 98.63 | 98.66 | 98.48 |
| | 6 mth | Homogenous | Homogenous | Homogenous | 7.58 | 7.60 | 7.48 | 98.44 | 98.84 | 98.43 |
| | 9 mth | — | Homogenous | — | — | 7.45 | — | — | 98.63 | — |
| | 12 mth | — | Homogenous | — | — | 7.30 | — | — | 98.42 | — |
| Example 12 | 0 mth | Homogenous | Homogenous | Homogenous | 8.03 | 7.96 | 7.88 | 99.03 | 98.69 | 98.42 |
| | 1 mth | Homogenous | Homogenous | Homogenous | 7.98 | 7.88 | 7.85 | 98.72 | 98.77 | 98.68 |
| | 2 mth | Homogenous | Homogenous | Homogenous | 7.78 | 7.75 | 7.73 | 98.33 | 98.64 | 98.84 |
| | 3 mth | Homogenous | Homogenous | Homogenous | 7.72 | 7.68 | 7.65 | 98.34 | 98.58 | 98.62 |
| | 6 mth | Homogenous | Homogenous | Homogenous | 7.55 | 7.47 | 7.41 | 98.65 | 98.79 | 98.79 |
| | 9 mth | — | Homogenous | — | — | 7.42 | — | — | 98.99 | — |
| | 12 mth | — | Homogenous | — | — | 7.36 | — | — | 98.45 | — |
| Example 16 | 0 mth | Homogenous | Homogenous | Homogenous | 7.96 | 7.84 | 7.94 | 99.62 | 98.64 | 98.41 |
| | 1 mth | Homogenous | Homogenous | Homogenous | 7.90 | 7.80 | 7.78 | 98.54 | 98.84 | 98.89 |
| | 2 mth | Homogenous | Homogenous | Homogenous | 7.84 | 7.76 | 7.68 | 98.80 | 98.62 | 99.03 |
| | 3 mth | Homogenous | Homogenous | Homogenous | 7.75 | 7.71 | 7.60 | 98.67 | 98.87 | 98.74 |
| | 6 mth | Homogenous | Homogenous | Homogenous | 7.60 | 7.58 | 7.24 | 98.43 | 98.59 | 98.66 |
| | 9 mth | — | Homogenous | — | — | 7.51 | — | — | 98.44 | — |
| | 12 mth | — | Homogenous | — | — | 7.29 | — | — | 98.63 | — |

As shown in Table 1, the lipid microspheres of this invention have good stability. No significant change to their appearance and encapsulation efficiency was noticed after being placed at 4° C. for 6 months followed by 45° C. for 6 months and, subsequently, placed at room temperature for 12 months. Although there were some degrees of decrease in pH, this did not affect the stability of the preparations.

Although the above only listed the results for the embodiments in this part of the specification, it should be noted that other embodiments of this invention also possess the same or similar beneficial effects.

In conclusion, lipid microsphere preparations prepared according to this invention possessed good stability which met the requirements on the stability of preparations stipulated in China's National Guidelines on Novel Drug Research.

Experiment 2

Method for Quality Control

The biphenol content in this invention was determined by high performance liquid chromatography. A C18 column (4.6 mm×200 mm, 5 μm) was used with methanol-acetonitrile-water (60:22:18) as the mobile phase at a flow rate of 1.0 ml/min and UV detection at 275 nm. The results showed that the average recovery rate was 99.35% with RSD=0.75% (n=11). Good linear relationship (r=0.9999) was found between concentration and the area under the peak for biphenol in the range 1~100 μg/ml.

Experiment 3

Determining the Encapsulation Efficiency of the Lipid Microsphere Preparations Lipid microsphere preparations were centrifuged at 10000 r/min for 30 minutes by ultracentrifugation. 0.5 ml of the supernatant was obtained and dissolved with isopropyl alcohol and the biphenol content was characterized with high performance liquid chromatography to determine the encapsulated biphenol content, $M_1$. The total biphenol content in lipid microsphere preparation is $M_0$. The following formula was used for calculating the encapsulation efficiency Q which is the weight ratio of biphenol lipid microspheres to biphenol.

$$Q = M_1/M_0 \times 100\%$$

The results showed that the encapsulation efficiency of the lipid microsphere preparation for intravenous injection prepared in this invention is greater than 98% when using biphenol as an indicator.

Experiment 4

Sterility Test

Sterility test was conducted on the lipid microsphere preparations of this invention in accordance to the method described in the appendix of the Chinese Pharmacopoeia 2010 edition. All lipid microsphere preparations of this invention passed the sterility test.

Experiment 5

Pyrogen Test

Pyrogen test was conducted on the lipid microsphere preparations of this invention in accordance to the method described in the appendix of the Chinese Pharmacopoeia 2010 edition. All lipid microsphere preparations of this invention passed the pyrogen test.

Experiment 6

Allergy Test

Method:
Three groups of 8 guinea pigs were randomly separated based on their weight. Each of the guinea pigs from group 1 and group 2 was given 3 successive peritoneal injections of the biphenol lipid microsphere preparations at a dose of 0.5 ml/guinea pig every other day to induce sensitization. On day 14 and day 21 after the first peritoneal injection, guinea pigs from groups 1 and 2 were given intravenous injections of the biphenol lipid microsphere preparations at the toe at a dose of 1.0 ml/guinea pig so as to cause stimulation. For group 3, the guinea pigs were given 3 successive peritoneal injections of 20% egg white at a dose of 0.5 ml/guinea pig every other day to induce sensitization and, after 14 days, were given intravenous injection of egg white at the toe at a dose of 1.0 ml/guinea pig so as to cause stimulation. All three groups were observed for 15 minutes after injection to notice for allergic reactions.

Results:
The two groups of guinea pigs injected with biphenol lipid microspheres which received the stimulation dose of same drug on day 14 and day 21 respectively did not show any allergic response. The guinea pigs in the positive control group had breathing difficulty and spasm within 2 minutes after injection before they died. The death of the guinea pigs were within 1~3 minutes after injection.

Conclusion:
The biphenol lipid microsphere preparation did not cause allergic reaction to guinea pigs under the current set of experimental conditions.

Experiment 7

Hemolysis Test

Method:
0.1 ml, 0.2 ml, 0.3 ml 0.4 ml and 0.5 ml of biphenol lipid microsphere preparations were separately added to 5 test tubes and diluted with 10% sucrose injection to 2.5 ml. 2.5 ml of 10% sucrose injection was added to a sixth test tube. 2.5 ml of distilled water was added to a seventh test tube (Control for complete hemolysis). 2.5 ml of 2% rabbit red blood cell suspension was added to each test tube and gently shaken before being placed in a 37° C. water bath. The hemolysis and coagulation in each test tube was recorded at 15 min, 30 min, 45 min, 1 h, 2 h, 3 h, and 4 h.

Results:
The five test tubes with biphenol lipid microsphere preparations did not cause hemolysis or coagulation in 4 hours.

Conclusion:
The biphenol lipid microsphere preparation did not cause hemolysis and coagulation under the current set of experimental conditions.

Experiment 8

Irritation Test

Method:
Biphenol lipid microsphere preparations were intravenously injected at the left ear of 2 New Zealand white rabbits at a dose of 5 ml/kg while 10% sucrose injections were intravenously injected at the right ear at a dose of 5 ml/kg. The injections were given daily for a total of five days. The injection site was observed for any swelling or rashes since day 1. Within 24 hours after the last injection, the ears were removed and fixed in 10% formalin before being prepared for histopathological examination.

Results:
No rashes or swelling was observed on both rabbit ears that were injected with biphenol lipid microsphere preparation daily for consecutive 5 days. Histopathologically, the epidermises of the rabbit ears appeared normal. No inflammatory cells or blood were exudating in the papillary layer and reticular layer. There were also no blood clots formed in the blood vessels and other structures also appeared normal.

Conclusion:
The biphenol lipid microsphere preparation had no irritation effect on the veins of the rabbit ear.

The following animal model experiments characterized the anti-epileptic effects of the lipid microsphere preparation prepared in accordance to above description.

In this experiment, there were 5 groups of 20 Kunming mice each namely, model group, control group (CMC-NA-biphenol group), drug test group 1, drug test group 2 and drug test group 3.

Experiment 1

Anti-Epileptic Effect of Different Concentrations of Biphenol Lipid Microsphere Preparations on PTZ Induced Seizures in Mice The mode of administration, type of drug and dose administered in each of the five groups are summarized in the following table. One hour after the drugs were administered, an intraperitoneal injection of PTZ (75 mg/kg) was used for inducing epileptic seizure. Results are summarized in the following table.

| Group | Mode of Administration | Type of Drug | Dose (mg/kg) | Seizure Severity | | | | | | Efficacy (≤III) |
|---|---|---|---|---|---|---|---|---|---|---|
| | | | | 0 | I | II | III | IV | V | |
| Model Group (n = 20) | Intravenous | Non-loaded lipid microspheres | 100 | 0 | 0 | 0 | 0 | 18 | 2 | 0% |
| Control Group (n = 20) | Gavage | CMCNa-biphenol | 100 | 0 | 0 | 0 | 2 | 18 | 0 | 10% |
| Drug Test Group 1 (n = 20) | Intravenous | Biphenol lipid microspheres | 100 | 20 | 0 | 0 | 0 | 0 | 0 | 100% |

-continued

| Group | Mode of Administration | Type of Drug | Dose (mg/kg) | 0 | I | II | III | IV | V | Efficacy (≤III) |
|---|---|---|---|---|---|---|---|---|---|---|
| Drug Test Group 2 (n = 20) | Intravenous | Biphenol lipid microspheres | 50 | 20 | 0 | 0 | 0 | 0 | 0 | 100% |
| Drug Test Group 3 (n = 20) | Intravenous | Biphenol lipid microspheres | 20 | 15 | 3 | 2 | 0 | 0 | 0 | 100% |

Seizure severity of the animal models was evaluated based on the Racine Stages (Stage 0 No response Stage I Mouth or facial rhythmic movement Stage II Head nodding or tail flicking Stage III Clonus of a single limb Stage IV Clonus or rearing in multiple limbs Stage V Full scale clonic-tonic seizure

Experiment 2

Anti-Epileptic Effect of Different Concentrations of Biphenol Lipid Microsphere Preparations on Bicuculline Induced Seizures in Mice The mode of administration, type of drug and dose administered in each of the five groups are summarized in the following table. One hour after the drugs were administered, a subdermal injection of Bic (2.7 mg/kg) was used for inducing epileptic seizure. Results are summarized in the following table.

| Group | Mode of Administration | Type of Drug | Dose (mg/kg) | 0 | I | II | III | IV | V | Efficacy (≤III) |
|---|---|---|---|---|---|---|---|---|---|---|
| Model Group (n = 20) | Intravenous | Non-loaded lipid microspheres | Equal Volume | 0 | 0 | 0 | 0 | 0 | 0 | 0% |
| Control Group (n = 20) | Gavage | CMCNa-biphenol | 100 | 0 | 0 | 0 | 0 | 4 | 4 | 40% |
| Drug Test Group 1 (n = 20) | Intravenous | Biphenol lipid microspheres | 100 | 20 | 0 | 0 | 0 | 0 | 0 | 100% |
| Drug Test Group 2 (n = 20) | Intravenous | Biphenol lipid microspheres | 50 | 12 | 1 | 2 | 3 | 2 | 0 | 100% |
| Drug Test Group 3 (n = 20) | Intravenous | Biphenol lipid microspheres | 20 | 10 | 2 | 3 | 4 | 1 | 0 | 100% |

Evaluation of bicuculline based model: The death rate for this model is 100%, therefore surivival after drug administration would indicate efficacy.

Experiment 3

Anti-Epileptic Effect of Different Concentrations of Biphenol Lipid Microsphere Preparations on 3-Mercaptopropionic Acid Induced Seizures in Mice The mode of administration, type of drug and dose administered in each of the five groups are summarized in the following table. One hour after the drugs were administered, a subdermal injection of 3-MP (60 mg/kg) was used for inducing epileptic seizure. Results are summarized in the following table.

| Group | Mode of Administration | Type of Drug | Dose (mg/kg) | 0 | I | II | III | Efficacy (≤III) |
|---|---|---|---|---|---|---|---|---|
| Model Group (n = 20) | Intravenous | Non-loaded lipid microspheres | Equal Volume | 0 | 0 | 0 | 20 | 0% |
| Control Group (n = 20) | Gavage | CMCNa-biphenol | 100 | 1 | 1 | 3 | 15 | 25% |
| Drug Test Group 1 (n = 20) | Intravenous | Biphenol lipid microspheres | 100 | 20 | 0 | 0 | 0 | 100% |
| Drug Test Group 2 (n = 20) | Intravenous | Biphenol lipid microspheres | 50 | 20 | 0 | 0 | 0 | 100% |
| Drug Test Group 3 (n = 20) | Intravenous | Biphenol lipid microspheres | 20 | 18 | 0 | 1 | 1 | 95% |

Evaluation of 3-mercaptopropionic acid based model: Stage I Incubation Stage II Clonic Seizure Stage III Tonic Seizure

Experiment 4

Anti-Epileptic Effect of Different Concentrations of Biphenol Lipid Microsphere Preparations on Maximal Electroshock Induced Seizures in Mice The mode of administration, type of drug and dose administered in each of the five groups are summarized in the following table. One hour after the drugs were administered, MES was used for inducing epileptic seizure. Results are summarized in the following table.

| Group | Mode of Administration | Type of Drug | Dose (mg/kg) | Seizure Severity No Seizure | Seizure | Efficacy (≤III) |
|---|---|---|---|---|---|---|
| Model Group (n = 20) | Intravenous | Non-loaded lipid microspheres | Equal Volume | 0 | 20 | 0% |
| Control Group (n = 20) | Gavage | CMCNa-biphenol | 100 | 2 | 18 | 10% |
| Drug Test Group 1 (n = 20) | Intravenous | Biphenol lipid microspheres | 100 | 18 | 2 | 90% |
| Drug Test Group 2 (n = 20) | Intravenous | Biphenol lipid microspheres | 50 | 15 | 5 | 75% |
| Drug Test Group 3 (n = 20) | Intravenous | Biphenol lipid microspheres | 20 | 12 | 8 | 60% |

Evaluation of maximal electroshock based model: Assessed based on whether the animal exhibited rigidity of all four limbs

Experiment 5

Anti-Epileptic Effect of Different Concentrations of Biphenol Lipid Microsphere Preparations on Penicillin Induced Seizures in Mice The mode of administration, type of drug and dose administered in each of the five groups are summarized in the following table. One hour after the drugs were administered, an intraperitoneal injection of penicillin (6 million U/kg) was used for inducing epileptic seizure. Results are summarized in the following table.

| Group | Mode of Administration | Type of Drug | Dose (mg/kg) | 0 | I | II | III | IV | V | Efficacy (≤III) |
|---|---|---|---|---|---|---|---|---|---|---|
| Model Group (n = 20) | Intravenous | Non-loaded lipid microspheres | 100 | 0 | 0 | 0 | 0 | 2 | 18 | 0% |
| Control Group (n = 20) | Gavage | CMCNa-biphenol | 100 | 0 | 1 | 2 | 1 | 3 | 13 | 20% |
| Drug Test Group 1 (n = 20) | Intravenous | Biphenol lipid microspheres | 100 | 18 | 2 | 0 | 0 | 0 | 0 | 100% |
| Drug Test Group 2 (n = 20) | Intravenous | Biphenol lipid microspheres | 50 | 18 | 1 | 1 | 0 | 0 | 0 | 100% |
| Drug Test Group 3 (n = 20) | Intravenous | Biphenol lipid microspheres | 20 | 15 | 2 | 0 | 1 | 1 | 1 | 90% |

Seizure severity of the animal models was evaluated based on the Racine Stages (Stage 0 No response Stage I Mouth or facial rhythmic movement Stage II Head nodding or tail flicking Stage III Clonus of a single limb Stage IV Clonus or rearing in multiple limbs Stage V Full scale clonic-tonic seizure Experimental results showed that the efficacy of biphenol lipid microsphere preparation improved several to dozens of times as compared to CMC-NA-biphenol.

It could be observed from the above results that the preparations of this invention are safe and reliable and do not induce any allergic, hemolytic or irritation effects. It therefore complies with the relevant requirements for clinically used drugs.

Although the above only selected the drug described in example 1 as the test drug, it should be noted that other embodiments of this invention also possess the same or similar beneficial effects.

The allergy test, hemolytic test and irritation test on the lipid microsphere preparations of this invention showed that the lipid microsphere preparations of this invention are highly stable and do not cause any allergic, hemolytic or irritation effects. It therefore complies with the relevant requirements for clinically used drugs.

What is claimed is:

1. A 2,2',6,6'-tetraisopropyl-4,4'-biphenol lipid microsphere preparation having 2,2',6,6'-tetraisopropyl-4,4'-biphenol as its active ingredient and formed into said lipid microsphere preparation with common medical use injection-grade oil, emulsifiers, and injection-grade water, wherein the chemical structure of said 2,2',6,6'-tetraisopropyl-4,4'-biphenol is:

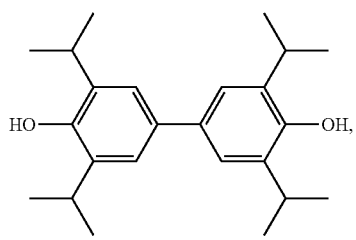 [SMILES: CC(C)c1cc(-c2cc(C(C)C)c(O)c(C(C)C)c2)cc(C(C)C)c1O]

wherein the preparation comprises 0.1-3 weight % of 2,2',6,6'-tetraisopropyl-4,4'-biphenol, 10-30 weight % of injection-grade oil, 1-1.5 weight % of emulsifier, 0.5-1 weight % antioxidants, 0-5 weight % additives and the remaining being injection-grade water;

wherein said injection-grade oil is selected from one or more of soybean oil, medium chain triglyceride oil, sea buckthorn oil and tea oil;

wherein said emulsifier is selected from one or more of soy lecithin, hydrogenated lecithin, synthetic phospholipid and egg lecithin;

wherein said antioxidant is selected from one or more of vitamin E, ascorbic acid and sodium bisulfite; and wherein said additive is selected from one or more of pH adjusting agent, tonicity adjusting agent and complexing agent.

2. The preparation of claim 1, wherein said pH adjusting agent is hydrochloric acid or sodium hydroxide; said tonicity adjusting agent is glycerin; said complexing agent is EDTA; wherein their composition is 0.01-1 weight %, 0.1-2.5 weight %, 0.01-1 weight % respectively.

3. The preparation of claim 1, wherein said lipid microsphere preparation is lipid microsphere preparation for intravenous injection.

4. The preparation of claim 1, wherein every 100 ml of said lipid microsphere preparation comprises 1000 mg of 2,2',6,6'-tetraisopropyl-4,4'-biphenol, 10 g of soybean oil, 1.2 g of injection grade egg lecithin, 1 g of vitamin E, 2.5 g glycerin, 0.5 g EDTA with the remaining being injection-grade water.

5. The preparation of claim 1, wherein the particle size of said lipid microsphere is distributed in the range 100 nm-800 nm with the average particle size being 150 nm-300 nm.

6. A method for preparing a biphenol lipid microsphere preparation comprising the steps of:
1) Dissolving an emulsifier completely with injection-grade oil under a nitrogen atmosphere and in a 70° C. water bath; adding antioxidants, with stirring for dissolution, before adding 2,2',6,6'-tetraisopropyl-4,4'-biphenol, with heat and stirring for dissolution, to obtain an oil phase;
2) Dissolving a tonicity adjusting agent and a complexing agent in injection-grade water to obtain an aqueous phase;
3) Adding the oil phase slowly to the aqueous phase while shearing under nitrogen for 5 minutes to obtain a preliminary emulsion; and
4) Homogenizing the preliminary emulsion with a high-pressure homogenizer and filtering with a microporous membrane filter before flushing with nitrogen, sealing and autoclaving at 115° C. to form the final product,
wherein the preparation comprises 0.1-3 weight % of 2,2',6,6'-tetraisopropyl-4,4'-biphenol.

7. A method for preparing a biphenol lipid microsphere preparation, comprising the steps of:
1) Weighing the raw materials: 1 g-30 g of 2,2',6,6'-tetraisopropyl-4,4'-biphenol, 100 ml-300 ml of injection-grade oil, 25 g of glycerin, 10 g-15 g of emulsifier, 5 g-10 g antioxidants, with the remaining being injection-grade water;
2) Dissolving the emulsifier and antioxidant completely with injection-grade oil under a nitrogen atmosphere and in a 70° C. water bath, before adding the biphenol, with heat and stirring for dissolution, to obtain an oil phase;
3) Dissolving the glycerin and the complexing agent in the injection-grade water, with stirring, to obtain an aqueous phase;
4) Adding the oil phase slowly to the aqueous phase while shearing under nitrogen (10000 r, 5 min) to obtain a preliminary emulsion, and adjusting pH to around 8.0 with NaOH; and
5) Homogenizing the preliminary emulsion 5-8 times with a high-pressure homogenizer at 800-900 bar and filtering with a microporous membrane filter before flushing with nitrogen, sealing and autoclaving at 115° C. to obtain the final product (1000 ml),
wherein the preparation comprises 0.1-3 weight % of 2,2',6,6'-tetraisopropyl-4,4'-biphenol.

8. A method for preparing biphenol lipid microsphere preparation comprising the steps of:
1) Weighing the raw materials: 1 g-30 g of 2,2',6,6'-tetraisopropyl-4,4'-biphenol, 100 ml-300 ml of injection-grade oil, 25 g of glycerin, 10 g-15 g of emulsifier, 5 g-10 g antioxidants, with the remaining being injection-grade water;
2) Dissolving the emulsifier and antioxidant completely with the injection-grade oil under a nitrogen atmosphere and in a 70° C. water bath before adding the biphenol, with heat and stirring for dissolution, to obtain an oil phase;
3) Dissolving the glycerin, antioxidant (ascorbic acid or sodium bisulfite) and complexing agent in the injection-grade water, with stirring, to obtain an aqueous phase;
4) Adding the oil phase slowly to the aqueous phase while shearing under nitrogen (10000 r, 5 min) to obtain a preliminary emulsion, and adjusting pH to around 8.0 with NaOH; and
5) Homogenizing the preliminary emulsion 5-8 times with a high-pressure homogenizer at 800-900 bar, filtering with a microporous membrane filter, filling with nitrogen, sealing and autoclaving at 115° C. to obtain the final product (1000 ml),
wherein the preparation comprises 0.1-3 weight % of 2,2',6,6'-tetraisopropyl-4,4'-biphenol.

* * * * *